US011698429B2

(12) United States Patent
Miyazaki

(10) Patent No.: US 11,698,429 B2
(45) Date of Patent: Jul. 11, 2023

(54) MRI T1 IMAGE-GUIDED TISSUE DIAGNOSTICS

(71) Applicant: Toshiba Medical Systems Corporation, Otawara (JP)

(72) Inventor: Mitsue Miyazaki, Mount Prospect, IL (US)

(73) Assignee: TOSHIBA MEDICAL SYSTEMS CORPORATION, Tochigi-Ken (JP)

( * ) Notice: Subject to any disclaimer, the term of this patent is extended or adjusted under 35 U.S.C. 154(b) by 504 days.

(21) Appl. No.: 16/390,652

(22) Filed: Apr. 22, 2019

(65) Prior Publication Data

US 2019/0250232 A1    Aug. 15, 2019

Related U.S. Application Data

(62) Division of application No. 12/923,891, filed on Oct. 13, 2010, now Pat. No. 10,267,882.

(51) Int. Cl.
*G01R 33/56*   (2006.01)
*A61B 5/055*   (2006.01)
*G01R 33/50*   (2006.01)

(52) U.S. Cl.
CPC .......... *G01R 33/5608* (2013.01); *A61B 5/055* (2013.01); *G01R 33/50* (2013.01)

(58) Field of Classification Search
CPC ................................................... G01R 33/50
See application file for complete search history.

(56) References Cited

U.S. PATENT DOCUMENTS

| 3,789,832 | A | 2/1974 | Damadian |
| 4,698,593 | A | 10/1987 | Crooks |
| 5,332,968 | A * | 7/1994 | Brown ................. G01R 33/563 324/309 |
| 6,009,342 | A | 12/1999 | Brasch et al. |
| 6,674,880 | B1 | 1/2004 | Stork et al. |
| 6,804,384 | B2 | 10/2004 | Lowen |

(Continued)

FOREIGN PATENT DOCUMENTS

| CN | 1973211 A | 5/2007 |
| JP | 2000-166897 A | 6/2000 |

(Continued)

OTHER PUBLICATIONS

Office Action dated Oct. 2, 2018 in U.S. Appl. No. 15/793,564.
(Continued)

*Primary Examiner* — James M Kish
(74) *Attorney, Agent, or Firm* — Nixon & Vanderhye, PC

(57) ABSTRACT

An MR image especially useful for computer-guided diagnostics uses at least one programmed computer to acquire an MR-image of T1 values for a patient volume containing at least one predetermined tissue type having a respectively corresponding predetermined range of expected T1 values. A color-coded T1-image is generated from the MR-image by (a) assigning a first color or spectrum of colors to those pixels having a T1 value falling within a predetermined range of expected T1 values and (b) assigning a second color or spectrum of colors to those pixels having a T1 value falling outside a predetermined range of expected T1 values. The color-coded T1-image is then displayed for use in computer-aided diagnosis of patient tissue.

14 Claims, 3 Drawing Sheets

(56) References Cited

U.S. PATENT DOCUMENTS

| | | | |
|---|---|---|---|
| 7,155,043 | B2 | 12/2006 | Daw |
| 9,167,988 | B2 | 10/2015 | Miyazaki |
| 2002/0016543 | A1 | 2/2002 | Tyler |
| 2003/0095147 | A1* | 5/2003 | Daw .................... G01R 33/56 715/771 |
| 2005/0190955 | A1 | 9/2005 | Brown |
| 2006/0273790 | A1 | 12/2006 | Eggers et al. |
| 2008/0012563 | A1 | 1/2008 | Weiss et al. |
| 2008/0150532 | A1 | 6/2008 | Slavin et al. |
| 2008/0300482 | A1 | 12/2008 | Mlejnek et al. |
| 2009/0232410 | A1 | 9/2009 | Dahnke et al. |
| 2010/0103166 | A1 | 4/2010 | Wamtjes |
| 2012/0095320 | A1 | 4/2012 | Miyazaki |
| 2012/0155733 | A1* | 6/2012 | Wagenkenecht ...... G06T 11/005 382/131 |

FOREIGN PATENT DOCUMENTS

| | | |
|---|---|---|
| JP | 2003-325510 A | 11/2003 |
| JP | 2006-524084 A | 10/2006 |
| JP | 2007-536970 A | 12/2007 |
| JP | 2008-534044 A | 8/2008 |
| JP | 2009-512932 A | 3/2009 |
| JP | 2010-075549 A | 4/2010 |

OTHER PUBLICATIONS

Extended European Search Report dated Mar. 29, 2017 in EP 11832601.6.

Fantazzini et al., "Use of Magnetic Resonance Imaging for monitoring Parma dry-cured ham processing," Meat Science, Elsevier Science, GB, vol. 82, No. 2, Jun. 1, 2009, pp. 219-227.

Vrenken et al., "Voxel-Based Analysis of Quantitative T1 Maps Demonstrates That Multiple Sclerosis Acts throughout the Normal-Appearing White Matter," American Journal of Neuroradiology, vol. 27, Apr. 1, 2006, pp. 868-874.

Liu et al., "Multi-spectral Analysis of Relaxation Time Maps on Fetal Baboon Brains," Proceedings of the International Society for Magnetic Resonance in Medicine, ISMRM, 16th Scientific Meeting and Exhibition, Toronto, Canada, May 3-9, 2008, Apr. 19, 2008, p. 3378.

Alfano et al., "Evaluation of brain tumors using the R1, R2, PD domain," Proceedings of the International Society for Magnetic Resonance in Medicine, ISMRM, Twelfth Annual Scientific Meeting Aug. 14-20, 1993, New York, New York, USA, Aug. 14, 1993, p. 1468.

Office Action dated Jun. 23, 2015 in JP Application No. 2011-226172.

Office Action dated Jul. 11, 2014 in U.S. Appl. No. 13/649,636.

Office Action dated Dec. 18, 2013 in Chinese Application No. 201180003911.4.

International Search Report dated Dec. 20, 2011 in PCT/JP2011/073570.

R.L. Kamman, G.P. Stomp, H.J.C. Berendsen, "Unified Multiple-Feature Color Display for MR Images," Magnetic Resonance in Medicine, 1989, vol. 9, Issue 2, pp. 240-253.

Kuhl, et al., "Dynamic Breast MR Imaging: Are Signal Intensity Time Course Data Useful for Differential Diagnosis of Enhancing Lesions?," Radiology, vol. 211, No. 1, pp. 101-110 (Apr. 1999).

Kuhl, "The Current Status of Breast MR Imaging, Part I, Choice of Technique, Image Interpretation, Diagnostic Accuracy, and Transfer to Clinical Practice," Radiology, vol. 244, No. 2, pp. 356-378 (Aug. 2007).

Kuhl, "Current Status of Breast MR Imaging, Part 2, Clinical Applications," Radiology, vol. 244, No. 3, pp. 672-691 (Sep. 2007).

Breger, et al., "T1 and T2 Measurements on a 1.5-T Commercial MR Imager," Radiology, vol. 171, No. 1, pp. 273-276 (Apr. 1989).

De Bazelaire, et al., "MR Imaging Relaxation Times of Abdominal and Pelvic Tissues Measured in Vivo at 3.0 T: Preliminary Results," Radiology, vol. 230, No. 3, pp. 652-659 (Mar. 2004).

Stanisz, et al., "$T_1$, $T_2$ Relaxation and Magnetization Transfer in Tissue at 3T," Magnetic Resonance in Medicine, vol. 54, pp. 507-512 (2005).

Kamman et al., "Unified Multiple-Feature Color Display for MR Images". Magnetic Resonance in Medicine 9, (1989), pp. 240-253.

Scheffler et al., "T1 Quantification With Inversion Recovery TrueFISP". Magnetic Resonance in Medicine 45: (2001), pp. 720-723.

Mosher et al., "Cartilage MRI T2 Relaxation Time Mapping: Overview and Applications". Seminars in Musculoskeletal Radiology, vol. 8, No. 4, 2004, pp. 355-368.

Detsky et al., "Reproducible Classification of Infarct Heterogeneity Using Fuzzy Clustering on Multicontrast Delayed Resonance Images". IEEE Transactions on Medical Imaging, vol. 28, No. 10, Oct. 2009, pp. 1606-1614.

Extended European Search Report in related corresponding European Appln. No. 11 832 601.6 dated Oct. 8, 2020.

Office Action in JP Application No. 2011-226172 dated Jul. 18, 2017.

European Patent Office in European Appln. No. 11 832 601.6 dated Feb. 16, 2022, 9 pages.

Brain Segmentation Performance Using T1-Weighted Images Versus T1 Maps from Department of Electrical and Computer Engineering, Virginia Tech, by Xiaoxing LI, et al., 9 pages.

European Patent Office in European Appln. No. 11 832 601.6 dated Feb. 13, 2023, 10 pages.

* cited by examiner

MRI T1 IMAGE-GUIDED TISSUE DIAGNOSTICS

CROSS-REFERENCE TO RELATED APPLICATIONS

This application is a divisional of Ser. No. 12/923,891 filed Oct. 13, 2010, the contents of which is hereby incorporated by reference.

FIELD

The subject matter below relates generally to magnetic resonance imaging (MRI) processes. Preferably, the MRI processes described below involve enhancements to T1 images of tissue for computer-aided diagnostics (CAD) of imaged patient tissue.

DETAILED DESCRIPTION

Figure 1:
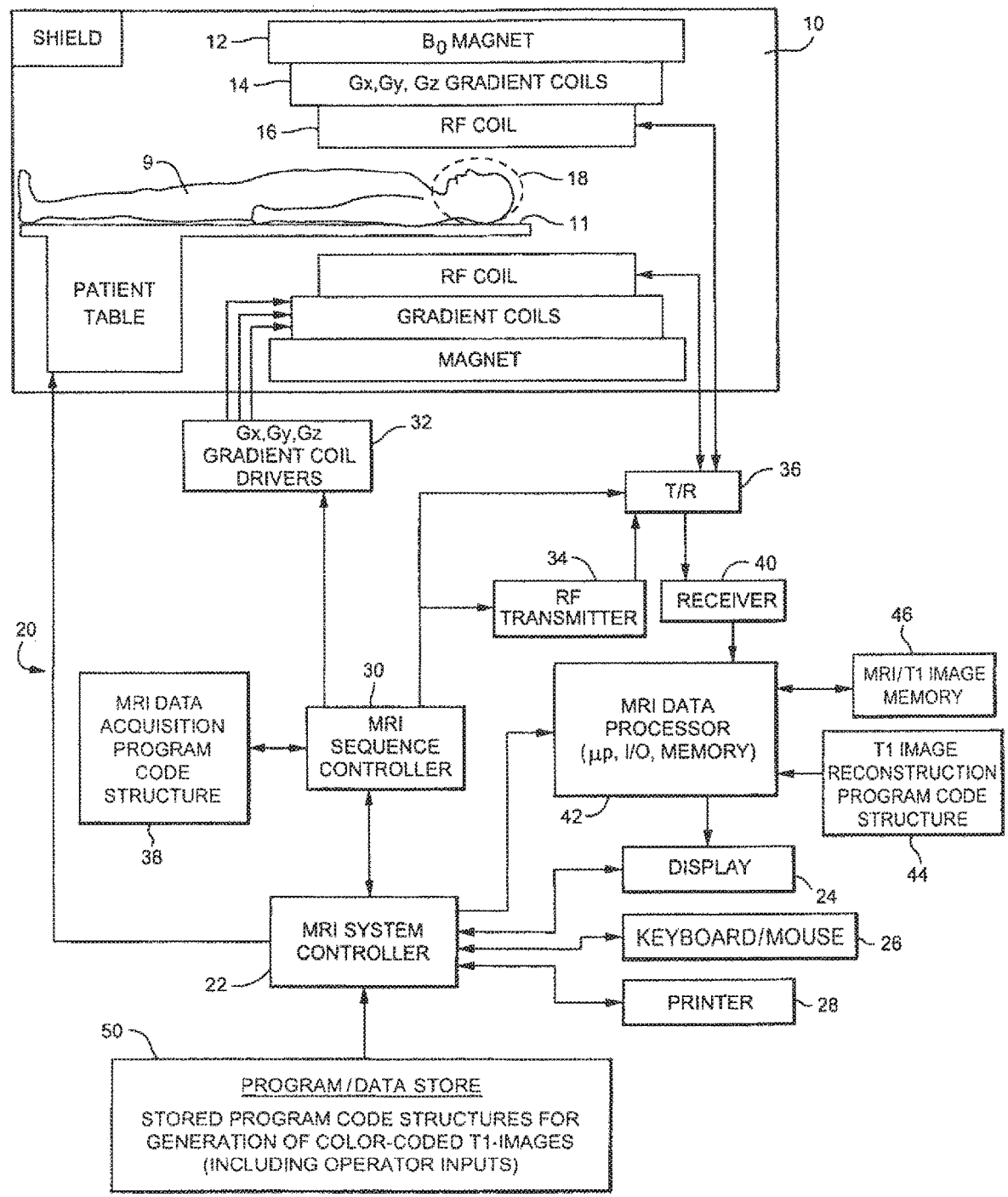
FIG. 1 is a high-level schematic block diagram of an MRI system adapted to acquire and process data for MRI using color-coding of T1 values in a T1 image to enhance computer-aided diagnosis.

The MRI system shown in FIG. 1 includes a gantry 10 (shown in schematic cross-section) and various related system components 20 interfaced therewith. At least the gantry 10 is typically located in a shielded room. One MRI system geometry depicted in FIG. 1 includes a substantially coaxial cylindrical arrangement of the static field B0 magnet 12, a $G_x$, $G_y$, and $G_z$ gradient coil set 14 and an RF coil assembly 16. Along the horizontal axis of this cylindrical array of elements is an imaging volume 18 shown as substantially encompassing the head of a patient 9 supported by a patient table 11.

An MRI system controller 22 has input/output ports connected to display 24, keyboard/mouse 26 and printer 28. As will be appreciated, the display 24 may be of the touch-screen variety so that it provides control inputs as well.

The MRI system controller 22 interfaces with MRI sequence controller 30 which, in turn, controls the $G_x$, $G_y$ and $G_z$ gradient coil drivers 32, as well as the RF transmitter 34 and the transmit/receive switch 36 (if the same RF coil is used for both transmission and reception). The MRI sequence controller 30 includes suitable program code structure 38 for implementing MRI data acquisition sequences already available in the repertoire of the MRI sequence controller 30 to generate T1-parameter valued image pixels (e.g., by capturing plural MR images at different TR intervals to calculate T1 values for each pixel in an image of tissue).

The MRI system 20 includes an RF receiver 40 providing input to data processor 42 so as to create processed image data to display 24. The MRI data processor 42 is also configured for access to T1-image reconstruction program code structure 44 and to MR T1 image memory 46 (e.g., for storing MR T1 image data derived from processing in accordance with the exemplary embodiments and the image reconstruction program code structure 44).

Also illustrated in FIG. 1 is a generalized depiction of an MRI system program/data store 50 where stored program code structures (e.g., for generation of color-coded T1-images, operator inputs to same, etc.) are stored in computer-readable storage media accessible to the various data processing components of the MRI system. As those in the art will appreciate, the program store 50 may be segmented and directly connected, at least in part, to different ones of the system 20 processing computers having most immediate need for such stored program code structures in their normal operation (i.e., rather than being commonly stored and connected directly to the MRI system controller 22).

Indeed, as those in the art will appreciate, the FIG. 1 depiction is a very high-level simplified diagram of a typical MRI system with some modifications so as to practice exemplary embodiments to be described hereinbelow. The system components can be divided into different logical collections of "boxes" and typically comprise numerous digital signal processors (DSP), microprocessors, special purpose processing circuits (e.g., for fast A/D conversions, fast Fourier transforming, array processing, etc.). Each of those processors is typically a clocked "state machine" wherein the physical data processing circuits progress from one physical state to another upon the occurrence of each clock cycle (or predetermined number of clock cycles).

Not only does the physical state of processing circuits (e.g., CPUs, registers, buffers, arithmetic units, etc.) progressively change from one clock cycle to another during the course of operation, the physical state of associated data storage media (e.g., bit storage sites in magnetic storage media) is transformed from one state to another during operation of such a system. For example, at the conclusion of an MR-imaging reconstruction process, an array of computer-readable accessible data value storage sites in physical storage media will be transformed from some prior state (e.g., all uniform "zero" values or all "one" values) to a new state wherein the physical states at the physical sites of such an array vary between minimum and maximum values to represent real world physical events and conditions (e.g., the tissues of a patient over an imaging volume space). As those in the art will appreciate, such arrays of stored data values represent and also constitute a physical structure—as does a particular structure of computer control program codes that, when sequentially loaded into instruction registers and executed by one or more CPUs of the MRI system 20, cause a particular sequence of operational states to occur and be transitioned through within the MRI system.

The exemplary embodiments described below provide improved ways to process data acquisitions and/or to generate and display MR-images.

Even if contrast materials are injected into a patient's imaged anatomy, thus highlighted MRI signals may still be missed when the image is used for diagnostic purposes. However, as may be ascertained from the following Table 1, different organs and/or tissues can be expected to have a wide range of differing T1 values (both at 1.5 Tesla and 3.0 Tesla imaging parameters). At the same time, as can be ascertained from the following Table 2, the MR T2 values for different tissue/organs may be relatively similar and with overlapping ranges that make it difficult to differentiate.

The following tables are taken from de Bazelaire, et al., "MR Imaging Relaxation Times of Abdominal and Pelvic Tissues Measured in Vivo at 3.0T: Preliminary Results," Radiology 230:3, pages 652-659, March 2004. As those in the art will appreciate, there are other sources of similar data readily available in the literature. For example, see Stanisz, et al, "$T_1$, $T_2$ Relaxation and Magnetization Transfer in Tissue at 3T," MRIM 54:507-512 (2005).

TABLE 1

Average T1 Relaxation Times at 1.5 Tesla and 3.0 Tesla

|  | 1.5 Tesla | | 3.0 Tesla | | |
| --- | --- | --- | --- | --- | --- |
| Tissue | T1 Relaxation Time (msec) | $R^2$ Value (%) | T1 Relaxation Time (msec) | $R^2$ Value (%) | Difference (%) |
| Kidney | | | | | |
| Cortex | 966 ± 58 | 0.999 | 1,142 ± 154 | 0.990 | 18 |
| Medulla | 1,412 ± 58 | 0.997 | 1,545 ± 142 | 0.999 | 9 |
| Liver | 586 ± 39 | 0.995 | 809 ± 71 | 0.987 | 38 |
| Spleen | 1,057 ± 42 | 0.998 | 1,328 ± 31 | 0.998 | 26 |
| Pancreas | 584 ± 14 | 0.982 | 725 ± 71 | 0.976 | 24 |
| Paravertebral muscle | 856 ± 61 | 0.988 | 898 ± 33 | 0.988 | 5 |
| Bone marrow (L4 vertebra) | 549 ± 52 | 0.991 | 586 ± 73 | 0.994 | 7 |
| Subcutaneous fat | 343 ± 37 | 0.997 | 382 ± 13 | 0.999 | 11 |
| Uterus | | | | | |
| Myometrium | 1,309 ± 35 | 0.998 | 1,514 ± 156 | 0.999 | 16 |
| Endometrium | 1,274 ± 64 | 0.997 | 1,453 ± 123 | 0.998 | 14 |
| Cervix | 1,135 ± 154 | 0.998 | 1,616 ± 61 | 0.998 | 42 |
| Prostate | 1,317 ± 85 | 0.999 | 1,597 ± 42 | 0.998 | 21 |

TABLE 2

Average T2 Relaxation Times at 1.5 Tesla and 3.0 Tesla

|  | 1.5 Tesla | | 3.0 Tesla | | |
| --- | --- | --- | --- | --- | --- |
| Tissue | T2 Relaxation Time (msec) | $R^2$ Value (%) | T2 Relaxation Time (msec) | $R^2$ Value (%) | Difference (%) |
| Kidney | | | | | |
| Cortex | 87 ± 4 | 0.993 | 76 ± 7 | 0.993 | −13 |
| Medulla | 85 ± 11 | 0.992 | 81 ± 8 | 0.996 | −5 |
| Liver | 46 ± 6 | 0.992 | 34 ± 4 | 0.984 | −26 |
| Spleen | 79 ± 15 | 0.998 | 61 ± 9 | 0.996 | −23 |
| Pancreas | 46 ± 6 | 0.989 | 43 ± 7 | 0.977 | −7 |
| Paravertebral muscle | 27 ± 8 | 0.925 | 29 ± 4 | 0.867 | 7 |
| Bone marrow (L4 vertebra) | 49 ± 8 | 0.997 | 49 ± 4 | 0.994 | 1 |
| Subcutaneous fat | 58 ± 4 | 0.995 | 68 ± 4 | 0.999 | 17 |
| Uterus | | | | | |
| Myometrium | 117 ± 14 | 0.995 | 79 ± 10 | 0.993 | −33 |
| Endometrium | 101 ± 21 | 0.987 | 59 ± 1 | 0.999 | −42 |
| Cervix | 58 ± 20 | 0.993 | 83 ± 7 | 0.992 | 43 |
| Prostate | 88 ± 0 | 0.997 | 74 ± 9 | 0.995 | −16 |

To provide improved computer-aided diagnostic (CAD) images in MRI (magnetic resonance imaging), especially for areas of the body outside intra-cranial MRA and breast tissues, images of T1-valued pixels can now be used to help guide differentiation between different tissues and/or organs. T1-weighted and/or T1-valued images can be obtained in various ways. For example, two or more MR images can be obtained with different TR intervals so as to permit exponential fitting processes to determine T1 values. Different inversion times (TI) can be used, as can different inversion recovery (IR) sequences or different values of TE (time to echo) so as to obtain requisite data for calculating T1 values (or at least T1-weighted values) for each pixel.

It is believed that a color-coded display of T1 values within a T1-image will make display of normal and irregular organ/tissue signals more easily differentiated by human eyes during diagnostic processes. In addition, rough ranges of expected T1 values using inversion recovery (IR) pulses can be accumulated over time to allow even better tissue characterization (e.g., so as to differentiate cancerous tumor cells from other tissues).

As shown by Table 1 above of published T1-parameter values for various tissues (including ranges of expected variation), it is possible to determine threshold ranges of T1 values so as to distinguish between various organs and/or tissues. It is now proposed that such ranges of T1 values be color-coded (e.g., with a given color for a certain range of T1 values or for a whole spectrum of colors to be assigned to a particular range of T1 values). Display of such color-coded images will permit one to achieve better visual recognition of a target organ/tissue even without the use of contrast agents. However, in addition, such color-coding of T1-valued images can be used in conjunction with contrast agents (e.g., which can be expected to further change the T1-parameter values for cancerous tumor tissues, as well as normal tissues).

Two or more T1-weighted images may be acquired so as to provide T1-image guides and/or reference images. A range of T1 values associated with a target organ/tissue may be used as a threshold range in which one or more colors are assigned to particular sub-ranges/values of the T1 parameter. For example, a first spectrum A of colors may be assigned to a first spectrum of T1-parameter values, while a second different spectrum B of color values may be assigned to a different spectrum of T1-parameter values (e.g., as might correspond to expected cancerous tissues that may be located within a target organ or body area).

If an injected contrast agent is to be utilized in conjunction with such color-coding of T1-valued images, then a CAD-guided image display may usefully be obtained both before and after the contrast injection so that comparisons may be made therebetween to enhance detection of possibly abnormal tissue.

If abnormal tissues are detected (e.g., possibly due to concentration of injected contrast agents or otherwise), then such abnormal T1-valued areas may be highlighted with a notable distinguishing color or color spectrum (e.g., a red-colored spectrum or possibly a single red color value).

An MRI system configured to provide such color-coded T1 image displays may provide a reference image of the same target area with conventional display parameters (e.g., contrast, gray scales, etc.). However utilized, it is believed that color-coded T1 images can provide a useful diagnostic tool for computer-aided diagnosis that better differentiates abnormal tissues from normal tissues based on such different tissues having respectively different T1-parameter values.

The set of color-coded T1-parameter valued images also can be used for CAD in conjunction with X-ray mammography and breast dynamic contrast enhancement (DCE).

Two or more T1-weighted images (or T1 with IR pulse) can be acquired to make the T1-valued guide or reference images. Different threshold ranges of T1 values can then be utilized to make corresponding color assignments to different ranges of T1 values. Such thresholding of ranges allows one to present tissue within a normal range in one color (or spectrum of colors) and abnormal signals in a different color (or spectrum of colors).

Besides published data showing ranges of T1 values to be expected for different tissues, a T1 range with rough T1 values can be expected due to the measurement methods, such as imaging sequences, B0 and/or B1 inhomogeneities, etc.

A CAD-guided image display taken before injection of contrast media may be compared to one taken after the injection of contrast media so as to better notice T1-parameter values then being displayed in different colors. As will be appreciated, the T1 value ranges for different abnormal tissues can be stored in system databases and used as reference data for identifying particular types of tumors or cancerous tissues.

Figure 2:
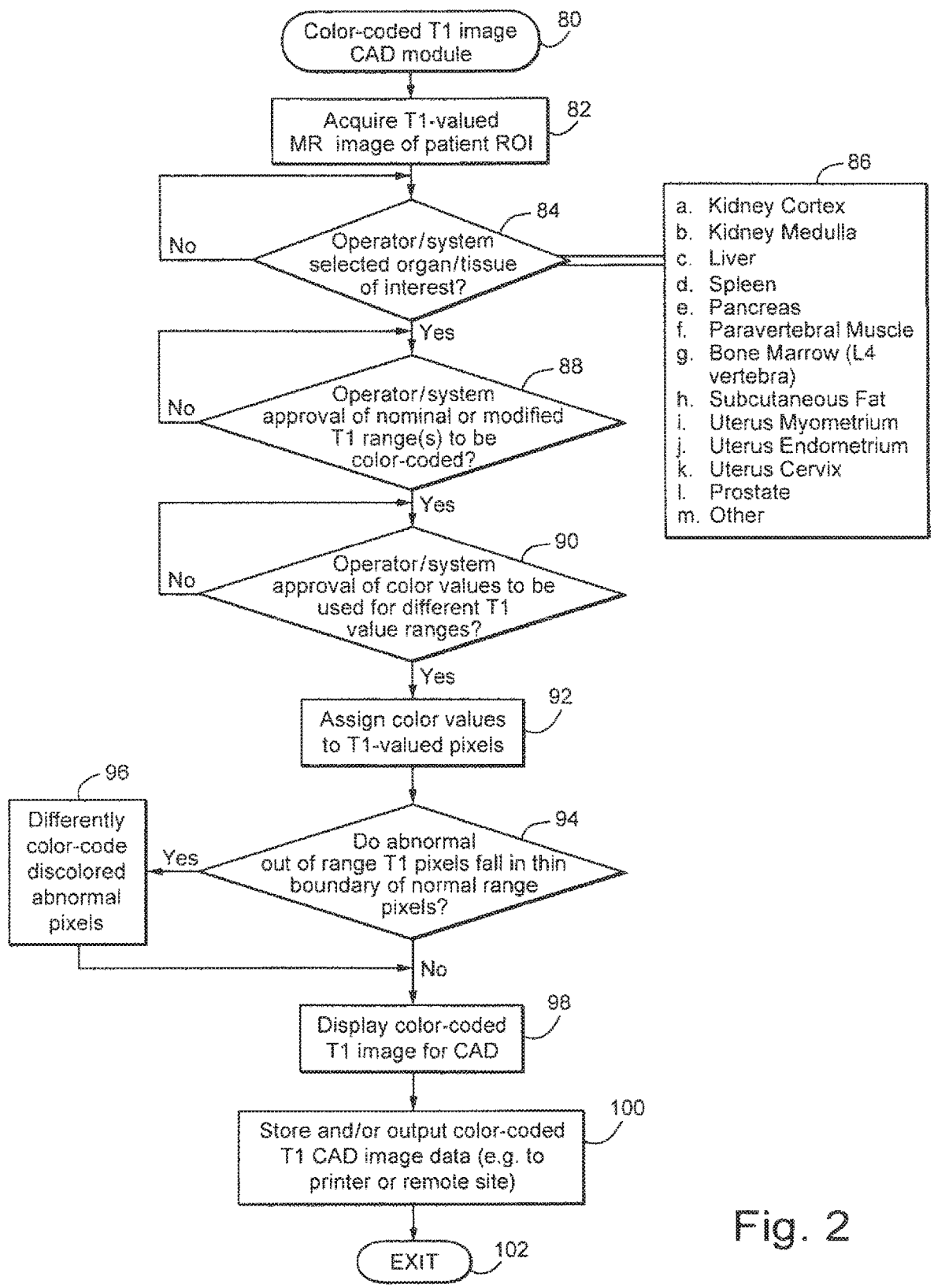
FIG. 2 is a schematic flow chart of exemplary computer program code structure that may be utilized for practicing an exemplary embodiment.

A color-coded T1-imaged CAD module as depicted in FIG. 2 may be entered at 80 by any suitable operator-entry or system-entry mode. For example, the operator might click on a mouse-selected icon, a touch-sensitive icon, a keyboard command or the like. Alternatively, the system may, in fact, select entry to this module based upon some other criteria.

At box 82, a T1-valued MR image of the patient region of interest (ROI) is acquired. Such a T1-valued image may be acquired by retrieving such from memory or may be originally acquired in real time by suitable MRI data acquisition using suitable MRI sequences, calculations, etc., so as to produce an MR image of the patient ROI having pixels with T1-values or at least T1-weighted values.

At decision box 84 in FIG. 2, a wait loop is entered, if necessary, to permit operator/system selection of an organ/ tissue of interest. For example, based on the entries in Table 1 noted above, the operator and/or system may have access to previously stored expected ranges of T1 values for many different organs and/or tissues of possible interest. Those pre-stored expected ranges of values may be used "as is". However, the operator/system may also have the option of modifying the ranges somewhat (e.g., so as to broaden or narrow the ranges and/or to weight the ranges in accordance with desired criteria). The operator/system may also have the option to select "other" as shown in box 86 where complete freedom is given to identify any desired particular range of T1 values that may be of interest for a particular target anatomy.

As already mentioned, the operator/system may have an option for approving the nominal or modified T1 ranges to be color-coded as depicted in the optional wait loop 88 of FIG. 2.

Similarly, the operator/system may have an optional wait loop 90 as indicated in FIG. 2 for approving and/or modifying color values, spectra, etc., to be used for different T1 values and/or ranges of values. At step 92, particular color values are assigned to particular T1-valued pixels. In conjunction therewith, or possibly before or after step 92, a test may be made as depicted at 94 in FIG. 2 for abnormal out-of-range T1-valued pixels (e.g., possibly being bounded by normal-valued ranges of pixels). If such abnormal collections of T1-valued pixels are discovered, then as depicted at 96, a different color (or color spectra) code may be assigned to such abnormal pixels.

As depicted at 98 in FIG. 2, the color-coded T1 image is displayed for CAD purposes. It may also be stored and/or output (e.g., to a printer or remote site) as depicted at 100 in FIG. 2 before exit from this module is taken at 102.

Figure 3:
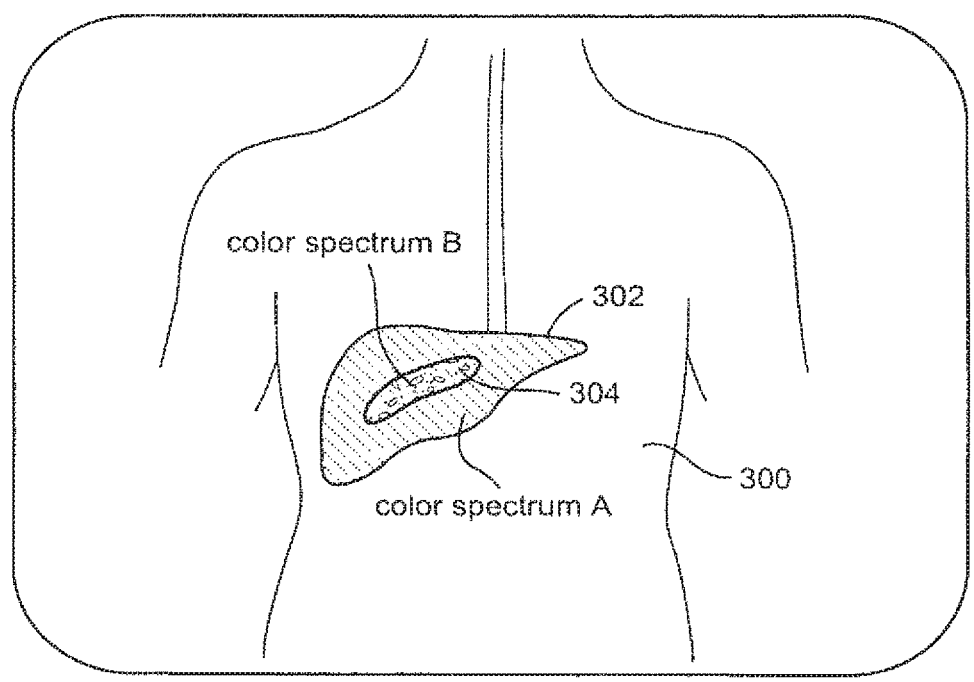
FIG. 3 is a schematic illustration of a possible screen display of an MRI T1 image showing a targeted organ that has been displayed with two distinguishable color spectra.

As a result of the module in FIG. 2, an image may be displayed as is schematically depicted at FIG. 3. Here, within the anatomy of a patient 300, an organ 302 is depicted with normal expected T1-valued pixels being assigned a color spectrum A. However, within the boundaries of organ 302, unexpected, abnormally valued pixels are discovered in area 304 and assigned a different contrasting color spectrum B. As explained previously, the system may be configured so as to permit the operator/system to assign different color spectra to different ranges of T1-valued pixels so as to optimize a CAD display for particular applications.

While certain embodiments of the inventions have been described, these embodiments have been presented by way of example only, and are not intended to limit the scope of the inventions. Indeed, the novel methods and systems described herein may be embodied in a variety of other forms. Furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

What is claimed is:

1. A computer-implemented method for generating a magnetic resonance (MR) image, said method comprising the use of at least one programmed computer to:
   analyze a plurality of MR images for a subject containing at least one organ or tissue type acquired using different inversion times as different imaging conditions, and derive quantitative values from signal intensities of pixels of the MR images by calculation of applying the signal intensities to an exponential function;
   in accordance with an operator input of selection of an organ or tissue type of interest, access a table in which a plurality of different organs or tissue types are respectively correlated to a plurality of predetermined ranges of quantitative values, and select the organ or tissue type of interest from among the plurality of different organs or tissue types, wherein the table is stored in a memory of the at least one programmed computer;
   modify the respective range of quantitative values correlated to the selected organ or tissue type of interest in the table in accordance with an operator input of modifying the respective range so as to broaden or narrow the range or to weight the range in accordance with desired criteria;
   in accordance with an operator input of determination of a specific color, assign the specific color to pixels of which the derived quantitative values are within the modified range to generate a color-coded image in which the selected organ or tissue type of interest is depicted with the specific color;
   when a pixel of an abnormal quantitative value that is out of a normal range of quantitative values of the organ or tissue type of interest is included in the pixels corresponding to the organ or tissue type of interest in the color-coded image, assign a color that is different from the specific color and that indicates abnormality to the pixel of the abnormal quantitative value; and
   display on a display the color-coded image.

2. The computer-implemented method as in claim 1, wherein said plurality of MR images are acquired by retrieval from a store of previously acquired MR images.

3. The computer-implemented method as in claim 1, wherein at least one of said plurality of MR images is acquired without administration of a contrast agent to said subject.

4. The computer-implemented method as in claim 1, wherein at least one of said plurality of MR images is acquired after administration of a contrast agent to said subject.

5. The computer-implemented method as in claim 1, wherein a first color-coded image is generated without administration of a contrast agent to said subject and a second color-coded image is generated with administration of a contrast agent in said subject, said first and second color-coded images constituting differently colorized images and wherein both said first and second color-coded images are concurrently displayed.

6. The computer-implemented method as in claim 1, wherein said plurality of MR images is obtained by using MRI data acquisition sequences employing different inversion times which are thereafter fitted to an exponential curve for each of respectively corresponding same pixels in said plurality of MR images thereby deriving a quantitative value for each pixel of a MR image.

7. The computer-implemented method as in claim 1, wherein at least one of said plurality of MR images is displayed as a reference image of said subject.

8. An apparatus for generating a magnetic resonance (MR) image, said apparatus comprising:
a memory configured to store a table in which a plurality of different organs or tissue types are respectively correlated to a plurality of predetermined ranges of quantitative values;
at least one processor configured to:
analyze a plurality of MR images for a subject containing at least one organ or tissue type acquired using different inversion times as different imaging conditions, and derive quantitative values from signal intensities of pixels of the MR images by calculation of applying the signal intensities to an exponential function;
in accordance with an operator input of selection of an organ or tissue type of interest, access the table stored in the memory, and select the organ or tissue type of interest from among the plurality of different organs or tissue types;
modify the respective range of quantitative values correlated to the selected organ or tissue type of interest in the table in accordance with an operator input of modifying the respective range so as to broaden or narrow the range or to weight the range in accordance with desired criteria;
in accordance with an operator input of determination of a specific color, assign the specific color to pixels of which the derived quantitative values are within the modified range to generate a color-coded image in which the selected organ or tissue type of interest is depicted with the specific color;
when a pixel of an abnormal quantitative value that is out of a normal range of quantitative values of the organ or tissue type of interest is included in the pixels corresponding to the organ or tissue type of interest in the color-coded image, assign a color that is different from the specific color and that indicates abnormality to the pixel of the abnormal quantitative value; and
display on a display the color-coded image.

9. The apparatus as in claim 8, wherein said plurality of MR images is acquired by retrieval from a store of previously acquired MR images.

10. The apparatus as in claim 8, wherein at least one of said plurality of MR images is acquired without administration of a contrast agent to said subject.

11. The apparatus as in claim 8, wherein at least one of said plurality of MR images is acquired after administration of a contrast agent to said subject.

12. The apparatus as in claim 8, wherein a first color-coded image is generated without administration of a contrast agent to said subject and a second color-coded image is generated with administration of a contrast agent in said subject, said first and second color-coded images constituting differently colorized images and wherein both said first and second color-coded images are concurrently displayed.

13. The apparatus as in claim 8, wherein said plurality of T1-weighted images is obtained by using MRI data acquisition sequences employing different inversion times which are thereafter fitted to an exponential curve for each of respectively corresponding same pixels in said plurality of MR images thereby deriving a quantitative value for each pixel of a MR image.

14. The apparatus as in claim 8, wherein at least one of said plurality of MR images is displayed as a reference image of said subject.

* * * * *